United States Patent [19]

Spaleck et al.

[11] Patent Number: 5,278,264
[45] Date of Patent: * Jan. 11, 1994

[54] PROCESS FOR THE PREPARATION OF AN OLEFIN POLYMER

[75] Inventors: Walter Spaleck, Liederbach; Jürgen Rohrmann, Kelkheim; Martin Antberg, Hofheim am Taunus, all of Fed. Rep. of Germany

[73] Assignee: Hoechst AG, Frankfurt, Fed. Rep. of Germany

[*] Notice: The portion of the term of this patent subsequent to Sep. 7, 2010 has been disclaimed.

[21] Appl. No.: 934,573

[22] Filed: Aug. 24, 1992

[30] Foreign Application Priority Data

Aug. 26, 1991 [DE] Fed. Rep. of Germany ....... 4128238

[51] Int. Cl.$^5$ .......................... C08F 2/06; C08F 4/64
[52] U.S. Cl. ................... 526/127; 526/160; 526/161; 526/351; 526/352; 502/117
[58] Field of Search ..................... 526/127, 160, 161

[56] References Cited

U.S. PATENT DOCUMENTS

| | | | |
|---|---|---|---|
| 4,769,510 | 9/1988 | Kaminsky et al. | |
| 5,001,205 | 3/1991 | Hoel | 526/160 |
| 5,081,322 | 1/1992 | Winter et al. | 526/160 |
| 5,120,867 | 6/1992 | Welborn, Jr. | 556/12 |
| 5,145,819 | 9/1992 | Winter et al. | 502/117 |

FOREIGN PATENT DOCUMENTS

| | | |
|---|---|---|
| 0344887 | 12/1989 | European Pat. Off. . |
| 0399348 | 11/1990 | European Pat. Off. . |
| 0433989 | 6/1991 | European Pat. Off. . |
| 0433990 | 6/1991 | European Pat. Off. . |
| 0485822 | 5/1992 | European Pat. Off. . |
| 0485823 | 5/1992 | European Pat. Off. . |
| 3826075 | 2/1990 | Fed. Rep. of Germany ...... 526/160 |
| 4035886 | 5/1992 | Fed. Rep. of Germany . |

OTHER PUBLICATIONS

Ewen, J. A. et al, *J. Am. Chem. Soc.* 109:6544–6545 (1987).

*Primary Examiner*—Joseph L. Schofer
*Assistant Examiner*—David Wu
*Attorney, Agent, or Firm*—Connolly and Hutz

[57] ABSTRACT

A very effective catalyst system for olefin polymerization consists of a cocatalyst, preferably an aluminoxane, and a metallocene of the formula (I)

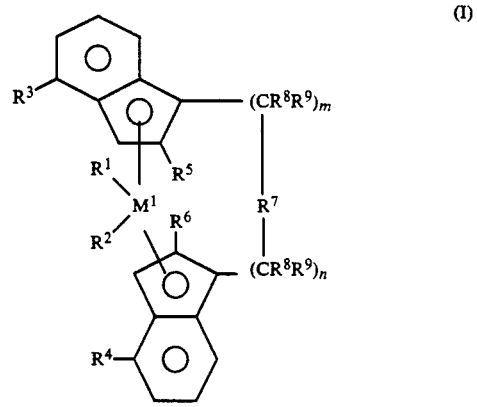

in which, preferably, $M^1$ is Zr, $R^1$ and $R^2$ are alkyl or halogen, $R^3$ to $R^6$ are alkyl, $-(CR^8R^9)_m-R^7-(CR^8R^9)_n-$ is a chain having one or more members, in which $R^7$ can also be a (substituted) hetero atom, and $m+n$ is zero or 1. The catalyst system leads to polymers of variable molecular weight and stereotacticity, depending on the substituents $R^3$ to $R^6$ chosen, at polymerization temperatures which are relevant in industry.

20 Claims, No Drawings

PROCESS FOR THE PREPARATION OF AN OLEFIN POLYMER

The present invention relates to a process for the preparation of olefin polymers having a narrow molecular weight distribution, variable molecular weight and, in the case of prochiral monomers, a variable microstructure of the chain.

Polyolefins of high molecular weight are of importance in particular for the production of films, sheets or hollow articles, such as, for example, pipes or moldings.

Polyolefins of low molecular weight are of importance for the preparation of additives or lubricants.

Soluble metallocene compounds based on bis(cyclopentadienyl)zirconium-alkyl or halide in combination with oligomeric aluminoxanes are known from the literature. Using these systems, it is possible to polymerize ethylene with a good activity and propylene with a moderate activity. Polyethylene of narrow molecular weight distribution and average molecular weight is obtained, and the polypropylene obtained is atactic and has a very low molecular weight.

Isotactic polypropylene is prepared with the aid of ethylene-bis(4,5,6,7-tetrahydro-1-indenyl)zirconium dichloride together with an aluminoxane in a suspension polymerization (cf. EP-A 185 918). The polymer has a narrow molecular weight distribution. A particular disadvantage of this process is, however, that only polymers of very low molecular weight can be prepared at polymerization temperatures which are of industrial interest.

A specific preactivation method for the metallocene with an aluminoxane has also been proposed, this leading to a considerable increase in the activity of the catalyst system and to a significant improvement in the particle morphology of the polymer (cf. DE-OS 37 26 067).

Catalysts based on ethylenebisindenylhafnium dichloride and ethylene-bis(4,5,6,7-tetrahydro-1-indenyl)hafnium dichloride and methylaluminoxane, with which higher molecular weight polypropylenes can be prepared by suspension polymerization, are furthermore known (cf. J. Am. Chem. Soc. 109 (1987) 6544). Under polymerization conditions which are relevant in industry, however, the particle morphology of the polymers produced in this way is not satisfactory and the activity of the catalysts employed is comparatively low. Together with the high catalyst costs, an inexpensive polymerization is therefore impossible using these systems.

The problems mentioned last are solved in principle by using bridged metallocene catalyst systems which carry an alkyl or aryl group in the 2-position relative to the bridge on the two aromatic ligands. Such systems are described in ZA 91/8925.

However, the catalysts mentioned last still have certain deficits in their properties or property combinations if a particularly broad applicability for various polymerization tasks and an industrially and economically favorable procedure is considered. In particular, it is desirable to carry out the polymerization at a high polymerization temperature, for example 70° C., because the catalyst activity is then high, and less cooling medium is needed to remove the heat of polymerization than at a low polymerization temperature, to be able to produce polyolefins of varying molecular weights at this high polymerization temperature without hydrogen having to be used as a molecular weight regulator (the polymers thus produced contain unsaturated end groups which can be used for chemical functionalizations), to be able to produce different stereotactic sequence lengths in stereospecific polymerization at this high polymerization temperature, these having the effect, for example in the case of isotactic polypropylene, of different melting points and other differences in properties, and to obtain a morphology of the polymer powder with average particle sizes of >1000 μm, since processing machines can be charged directly with such powders without granulation.

It has now been found that these objects can be achieved using bridged metallocenes which are substituted in a certain manner in the ligand sphere.

The invention thus relates to a process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$ form a ring with the atoms joining them, at a temperature of −60° to 200° C., under a pressure of 0.5 to 100 bar, in solution, in suspension or in the gas phase, in the presence of a catalyst which is formed from a metallocene as the transition metal compound and a cocatalyst, which comprises using as the metallocene a compound of the formula I

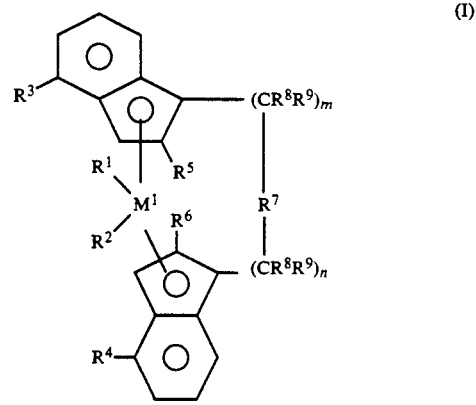

in which $M^1$ is a metal of group IVb, Vb or VIb of the Periodic Table, $R^1$ and $R^2$ are identical or different and are hydrogen, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group or a halogen atom, $R^3$ and $R^4$ are identical or different and are a halogen atom, a $C_1$-$C_{10}$-alkyl group, which can be halogenated, a $C_6$-$C_{10}$-aryl group or an —$NR_2^{10}$, —$SR^{10}$, —$OSiR_3^{10}$, —$SiR_3^{10}$ or —$PR_2^{10}$ radical, in which $R^{10}$ is a halogen atom, a $C_1$-$C_{10}$-alkyl group or a $C_6$-$C_{10}$-aryl group, $R^5$ and $R^6$ are identical or different and have the meaning mentioned for $R^3$ and $R^4$, and additionally can also be hydrogen, $R^7$ is

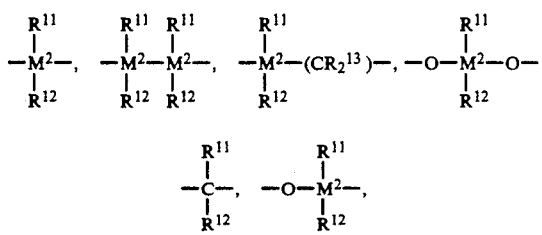

=BR$^{11}$, =AlR$^{11}$, —Ge—, —Sn—, —O—, —S—, =SO, =SO$_2$, =NR$^{11}$, =CO, =PR$^{11}$ or =P(O)R$^{11}$, in which R$^{11}$, R$^{12}$ and R$^{13}$ are identical or different and are a hydrogen atom, a halogen atom, a C$_1$-C$_{10}$-alkyl group, a C$_1$-C$_{10}$-fluoroalkyl group, a C$_6$-C$_{10}$-aryl group, a C$_6$-C$_{10}$-fluoroaryl group, a C$_1$-C$_{10}$-alkoxy group, a C$_2$-C$_{10}$-alkenyl group, a C$_7$-C$_{40}$-arylalkyl group, a C$_8$-C$_{40}$-arylalkenyl group or a C$_7$-C$_{40}$-alkylaryl group, or R$^{11}$ and R$^{12}$ or R$^{11}$ and R$^{13}$ in each case form a ring with the atoms joining them, or R$^{11}$ or R$^{12}$ with R$^8$ or R$^9$ in each case form a ring together with the atoms joining them, M$^2$ is silicon, germanium or tin, R$^8$ and R$^9$ are identical or different and have the meaning mentioned for R$^{11}$ and m and n are identical or different and are zero, 1 or 2, m plus n being zero, 1 or 2.

Alkyl is straight-chain or branched alkyl. Halogen (halogenated) is fluorine, chlorine, bromine or iodine, preferably fluorine or chlorine.

The present invention furthermore relates to the polyolefins prepared by the process described.

The catalyst to be used for the process according to the invention consists of a cocatalyst and a metallocene of the formula I

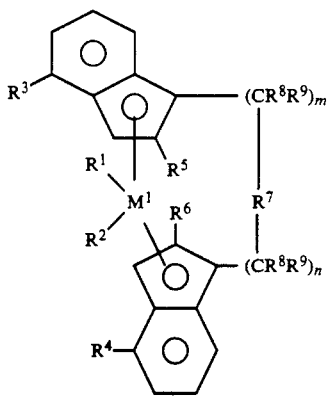

In formula I, M$^1$ is a metal of group IVb, Vb or VIb of the Periodic Table, for example titanium, zirconium, hafnium, vanadium, niobium, tantalum, chromium, molybdenum and tungsten, preferably zirconium, hafnium and titanium.

R$^1$ and R$^2$ are identical or different, preferably identical, and are a hydrogen atom, a C$_1$-C$_{10}$-, preferably C$_1$-C$_3$-alkyl group, a C$_1$-C$_{10}$-, preferably C$_1$-C$_3$-alkoxy group, a C$_6$-C$_{10}$-, preferably C$_6$-C$_8$-aryl group, a C$_6$-C$_{10}$-, preferably C$_6$-C$_8$-aryloxy group, a C$_2$-C$_{10}$-, preferably C$_2$-C$_4$-alkenyl group, a C$_7$-C$_{40}$-, preferably C$_7$-C$_{10}$-arylalkyl group, a C$_7$-C$_{40}$-, preferably C$_7$-C$_{12}$-alkylaryl group, a C$_8$-C$_{40}$-, preferably C$_8$-C$_{12}$-arylalkenyl group or a halogen atom, preferably chlorine.

R$^3$ and R$^4$ are identical or different, preferably identical, and are a halogen atom, preferably a chlorine, bromine or iodine atom, a C$_1$-C$_{10}$-, preferably C$_1$-C$_6$-alkyl group, which can be halogenated, a C$_6$-C$_{10}$-, preferably C$_6$-C$_8$-aryl group or an —NR$_2^{10}$, —SR$^{10}$, —OSiR$_3^{10}$, —SiR$_3^{10}$ or —PR$_2^{10}$ radical, in which R$^{10}$ is a halogen atom, preferably a chlorine atom, or a C$_1$-C$_{10}$-, preferably C$_1$-C$_3$-alkyl group or a C$_6$-C$_{10}$-, preferably C$_6$-C$_8$-aryl group.

R$^5$ and R$^6$ are identical or different, preferably identical, and have the meaning described for R$^3$ and R$^4$, with the proviso that R$^5$ and R$^6$ may also be hydrogen. R$^5$ and R$^6$ are preferably (C$_1$-C$_4$)-alkyl, which can be halogenated, such as methyl, ethyl, propyl, isopropyl, butyl, isobutyl or trifluoromethyl, in particular methyl and ethyl.

R$^7$ is

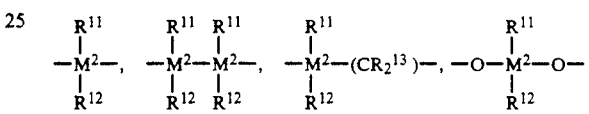

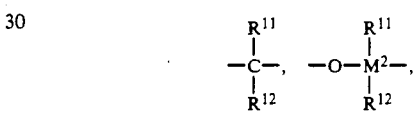

=BR$^{11}$, =AlR$^{11}$, —Ge—, —Sn—, —O—, —S—, =SO, =SO$_2$, =NR$^{11}$, =CO, =PR$^{11}$ or =P(O)R$^{11}$, in which R$^{11}$, R$^{12}$ and R$^{13}$ are identical or different and are a hydrogen atom, a halogen atom, a C$_1$-C$_{10}$-, preferably C$_1$-C$_4$-alkyl group, in particular a methyl group, a C$_1$-C$_{10}$-fluoroalkyl group, preferably a CF$_3$ group, a C$_6$-C$_{10}$-, preferably C$_6$-C$_8$-aryl group, a C$_6$-C$_{10}$-fluoroaryl group, preferably a pentafluorophenyl group, a C$_1$-C$_{10}$-, preferably C$_1$-C$_4$-alkoxy group, in particular a methoxy group, a C$_2$-C$_{10}$-, preferably C$_2$-C$_4$-alkenyl group, a C$_7$-C$_{40}$-, preferably C$_7$-C$_{10}$-arylalkyl group, a C$_8$-C$_{40}$-, preferably C$_8$-C$_{12}$-arylalkenyl group or a C$_7$-C$_{40}$-, preferably C$_7$-C$_{12}$-alkylaryl group, or R$^{11}$ and R$^{12}$ or R$^{11}$ and R$^{13}$ in each case form a ring together with the atoms joining them, or R$^{11}$ or R$^{12}$ with R$^8$ or R$^9$ in each case form a ring together with the atoms joining them.

M$^2$ is silicon, germanium or tin, preferably silicon and germanium.

R$^7$ is preferably =CR$^{11}$R$^{12}$, =SiR$^{11}$R$^{12}$, =GeR$^{11}$R$^{12}$, —O—, —S—, =SO, =PR$^{11}$ or =P(O)R$^{11}$.

R$^8$ and R$^9$ are identical or different and have the meaning mentioned for R$^{11}$.

m and n are identical or different and are zero, 1 or 2, preferably zero or 1, m plus n being zero, 1 or 2, preferably zero or 1.

The particularly preferred metallocenes are thus the compounds of the formulae A, B and C (A) 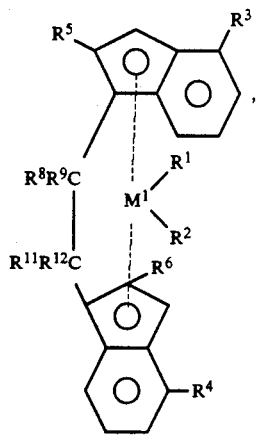

(B) 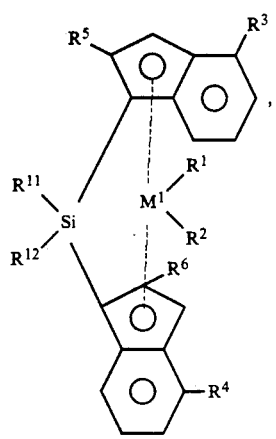

(C) 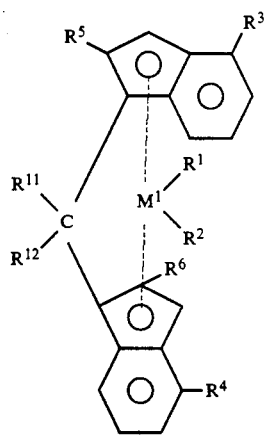

where
$M^1$=Zr, $R^1$ and $R^2$=methyl or chlorine; $R^3$ and $R^4$=methyl, ethyl, n-propyl, i-propyl, n-butyl, i-butyl, tert-butyl or neopentyl; $R^5$ and $R^6$=methyl or ethyl and $R^8$, $R^9$, $R^{11}$ and $R^{12}$ have the abovementioned meanings, in particular the compounds I mentioned in the examples.

The chiral metallocenes are employed as a racemate for the preparation of isotactic poly-1-olefins.

However, the pure R or S form can also be used. Optically active polymer can be prepared using these pure stereoisomer forms. However, the meso form of the metallocenes should be separated off, since the polymerization-active center (the metal atom) is no longer chiral in these compounds because of mirror symmetry on the central metal, and therefore cannot produce a highly isotactic polymer. If the meso form is not separated off, atactic polymer is also formed alongside isotactic polymer. This may be entirely desirable for certain uses—for example flexible shaped articles.

The separation of the stereoisomers is known in principle.

The metallocenes described above can be prepared in accordance with the following equation:

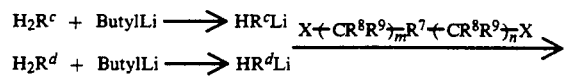

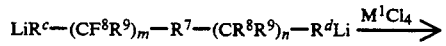

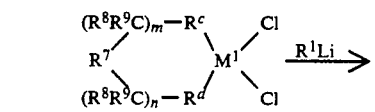

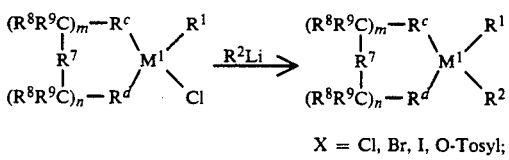

X = Cl, Br, I, O-Tosyl;

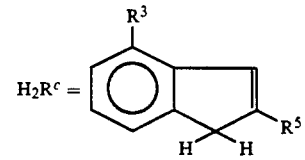

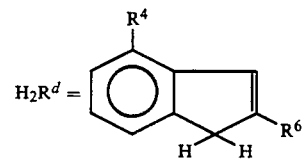

The preparation processes are known from the literature; cf. Journal of Organometallic Chem. 288 (1985) 63–67, EP-A 320 762 and the embodiment examples.

The 2,4-substituted indenes $H_2R^c$ and $H_2R^d$ used as starting substances can be prepared by 2 different routes.

a) A ketoaldehyde of the formula shown in the equation below, the preparation of which is known (Synthesis 1985, 1058), is used as the starting compound.

The reaction of this ketoaldehyde with cyclopentadiene is carried out in an inert solvent in the presence of a base. Alcohols, such as methanol, ethanol or t-butanol, in particular methanol, are preferably used.

A large number of compounds can be used as bases. Examples which may be mentioned are alkali metal and alkaline earth metal hydroxides, alkali metal and alkaline earth metal alcoholates, such as sodium methanolate, sodium ethanolate and potassium tert-butanolate, amides, such as lithium diisopropylamide, or amines. Sodium ethanolate, potassium tert-butanolate and potassium hydroxide are preferably used.

The molar ratios of the starting compounds, including the base used, can vary within wide limits. The molar ratio of ketoaldehyde:cyclopentadiene:base is preferably 1:1–1.5:2–3; in particular 1:1.1:2.5.

The reaction temperature is preferably −40° C. to 100° C., in particular 0° C.–25° C.

The reaction times as a rule vary between 10 minutes and 100 hours, preferably between 1 hour and 30 hours.

After conversion of the indene which is monosubstituted in the 4-position into the 2-indanone which is monosubstituted in the 4-position in accordance with general working instructions (Organic Synthesis, Coll. Vol. V, 1973, 647), the substituent in the 2-position can be introduced by a Grignard reaction. The subsequent splitting off of water leads to the 2,4-substituted indenes.

The 2,4-substituted indenes are obtained as double bond isomers, which can be employed directly for the synthesis of the corresponding metallocene complexes.

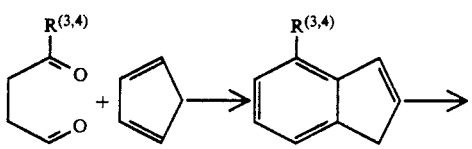

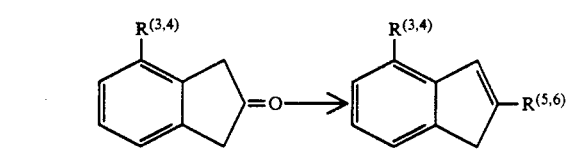

b) Another possible and advantageous strategy proceeds in accordance with the following plan:

A benzyl halide which is substituted in the 2-position is converted, by reaction with an appropriately substituted malonic acid diester by a process analogous to a process known from the literature (J. Org. Chem. 1958, 23, 1437), into the disubstituted malonic acid diester.

Hydrolysis of the diester and decarboxylation by customary processes leads to a disubstituted propionic acid derivative.

After conversion of the carboxylic acid into the carboxylic acid chloride, the cyclization to give the 2,4-disubstituted 1-indanone is carried out by customary processes.

Reduction of the ketone by known methods and subsequent splitting off of water gives the 2,4-disubstituted indenes.

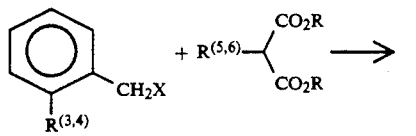

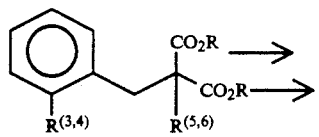

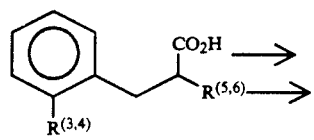

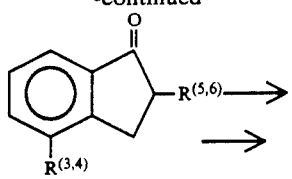

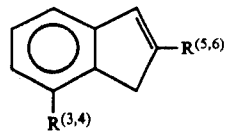

According to the invention, the cocatalyst used is preferably an aluminoxane of the formula (II)

$$R^{14}\!\!\diagdown_{\!\!\!Al}\!\!-O\!\!-\!\!\left[\begin{array}{c}R^{14}\\|\\Al\!-\!O\end{array}\right]_{\!p}\!\!-\!Al\diagup^{\!\!R^{14}}_{\!\!R^{14}} \quad \text{(II)}$$

for the linear type and/or of the formula (III)

$$\left[\!\!-\!\!O\!\!-\!\!\begin{array}{c}R^{14}\\|\\Al\end{array}\!\!-\!\!\right]_{\!p+2} \quad \text{(III)}$$

for the cyclic type, in which, in the formulae (II) and (III), the radicals $R^{14}$ can be identical or different and are a $C_1$–$C_6$-alkyl group, a $C_6$–$C_{18}$-aryl group or hydrogen and p is an integer from 2 to 50, preferably 10 to 35.

The radicals $R^{14}$ are preferably identical and are methyl, isobutyl, phenyl or benzyl, particularly preferably methyl.

If the radicals $R^{14}$ differ, they are preferably methyl and hydrogen, or alternatively methyl and isobutyl, hydrogen or isobutyl preferably being contained in the compounds to the extent of 0.01–40% (number of radicals $R^{14}$).

The aluminoxane can be prepared in various manners by known processes. One of the methods is, for example, to react an aluminum-hydrocarbon compound and/or a hydrido-aluminum-hydrocarbon compound with water (gaseous, solid, liquid or bonded—for example as water of crystallization) in an inert solvent (such as, for example, toluene). To prepare an aluminoxane having different alkyl groups $R^{14}$, two different aluminum-trialkyls ($AlR_3 + AlR'_3$), corresponding to the desired composition, are reacted with water (cf. S. Pasynkiewicz, Polyhedron 9 (1990) 429 and EP-A 302 424).

The precise structure of the aluminoxanes II and III is not known.

Regardless of the nature of their preparation, all aluminoxane solutions have the common feature of a varying content of unreacted aluminum starting compound, which is present in the free form or as an adduct.

It is possible for the metallocene to be preactivated with an aluminoxane of the formula (II) and/or (III) before use in the polymerization reaction. This significantly increases the polymerization activity and improves the particle morphology.

The preactivation of the transition metal compound is carried out in solution. Preferably, for this operation, the metallocene is dissolved in a solution of the aluminoxane in an inert hydrocarbon. An aliphatic or aromatic hydrocarbon is suitable as an inert hydrocarbon. Toluene is preferably used.

The concentration of the aluminoxane in the solution is in the range from about 1% by weight to the saturation limit, preferably from 5 to 30% by weight, in each case based on the total solution. The metallocene can be employed in the same concentration, but it is preferably employed in an amount of $10^{-4}$-1 mol per mole of aluminoxane. The preactivation time is 5 minutes to 60 hours, preferably 5 to 60 minutes. The preactivation is carried out at a temperature of $-78°$ C. to $100°$ C., preferably $0°$ to $70°$ C.

The metallocene can also be prepolymerized or applied to a support. The (or one of the) olefins employed in the polymerization are (or is) preferably used for the prepolymerization.

Suitable supports are, for example, silica gels, aluminum oxides, solid aluminoxane or other inorganic support materials. A polymer powder in finely divided form is also a suitable support material.

According to the invention, compounds of the formulae $R_xNH_{4-x}BR'_4$, $R_xPH_{4-x}BR'_4$, $R_3CBR'_4$ or $BR'_3$ can be used as suitable cocatalysts instead of or in addition to an aluminoxane. In these formulae, x is a number from 1 to 4, preferably 3, the radicals R are identical or different, preferably identical, and are $C_1$-$C_{10}$-alkyl or $C_6$-$C_{18}$-aryl, or 2 radicals R form a ring together with the atom joining them, and the radicals R' are identical or different, preferably identical, and are $C_6$-$C_{18}$-aryl, which can be substituted by alkyl, haloalkyl or fluorine.

In particular, R is ethyl, propyl, butyl or phenyl, and R' is phenyl, pentafluorophenyl, 3,5-bistrifluoromethylphenyl, mesityl, xylyl or tolyl (cf. EP-A 277 003, EP-A 277 004 and EP-A-426 638).

If the abovementioned cocatalysts are used, the actual (active) polymerization catalyst comprises the reaction product of the metallocene and one of the compounds mentioned. This reaction product is therefore preferably prepared first outside the polymerization reactor in a separate step using a suitable solvent (cf. Embodiment Example VIII).

In principle, any compound which, on the basis of its Lewis acidity, can convert the neutral metallocene into a cation and stabilize it ("labile coordination") is suitable according to the invention as a cocatalyst. Moreover, the cocatalyst or the anion formed from it should not undergo any further reactions with the metallocene cation formed (cf. EP-A 427 697).

To remove catalyst poisons present in the olefin, purification with an aluminum-alkyl, for example $AlMe_3$ or $AlEt_3$, is advantageous. This purification can either be carried out in the polymerization system itself, or the olefin is brought into contact with the Al compound before addition into the polymerization system and is subsequently separated off again.

The polymerization or copolymerization is carried out in a known manner in solution, in suspension or in the gas phase continuously or discontinuously, in one or more stages, at a temperature of $-60°$ to $200°$ C., preferably $30°$ to $80°$ C. Olefins of the formula $R^a$—CH=CH—$R^b$ are polymerized or copolymerized. In this formula, $R^a$ and $R^b$ are identical or different and are a hydrogen atom or an alkyl radical having 1 to 14 C atoms. However, $R^a$ and $R^b$ can also form a ring with the C atoms joining them. Examples of such olefins are ethylene, propylene, 1-butene, 1-hexene, 4-methyl-1-pentene, 1-octene, norbornene or norbornadiene. Propylene and ethylene are polymerized in particular.

Hydrogen is added as a molecular weight regulator, if necessary. The total pressure in the polymerization system is 0.5 to 100 bar. Polymerization in the pressure range from 5 to 64 bar, which is of particular industrial interest, is preferred.

The metallocene is used in this polymerization in a concentration, based on the transition metal, of $10^{-3}$ to $10^{-8}$, preferably $10^{-4}$ to $10^{-7}$ mol of transition metal per $dm^3$ of solvent or per $dm^3$ of reactor volume. The aluminoxane is used in a concentration of $10^{-5}$ to $10^{-1}$ mol, preferably $10^{-4}$ to $10^{-2}$ mol per $dm^3$ of solvent or per $dm^3$ of reactor volume. The other cocatalysts mentioned are used in amounts which are approximately equimolar to that of the metallocene. In principle, however, higher concentrations are also possible.

If the polymerization is carried out as suspension or solution polymerization, an inert solvent customary for the Ziegler low pressure process is used. For example, the polymerization is carried out in an aliphatic or cycloaliphatic hydrocarbon; examples of such solvents which may be mentioned are propane, butane, pentane, hexane, heptane, isooctane, cyclohexane and methylcyclohexane. A gasoline or hydrogenated diesel oil fraction can furthermore be used. Toluene can also be used. The polymerization is preferably carried out in the liquid monomer.

If inert solvents are used, the monomers are metered in as gases or liquids.

The polymerization time can be chosen as desired, since the catalyst system to be used according to the invention shows only a slight time-dependent drop in polymerization activity.

The process according to the invention is distinguished by the fact that the metallocene catalyst systems described produce polymers having a narrow molecular weight distribution and coarse particle morphology as well as variable molecular weight and stereotacticity in the temperature range between $30°$ and $80°$ C., which is of industrial interest, but in particular in the range between $60°$ and $80°$ C. The particular polymer molecular weight and stereotacticity desired is established by choosing suitable substituents in the 2- and 4-positions of the ligand system of the metallocene. If the polymerization is carried out without hydrogen as a molecular weight regulator, the polymers contain unsaturated end groups.

The following examples are intended to illustrate the invention in more detail.

In the examples:

$VN$ = viscosity number in $cm^3/g$ $M_w$ = weight-average molecular weight in g/mol ⎫
$M_w/M_n$ = molecular weight dispersity ⎬ determined by gel permeation chromatography ⎭ m.p. = melting point, determined by DSC ($20°$ C./minute heating up/cooling rate)

II = isotactic index (II=mm+½ mr) determined by $^{13}$C-NMR spectroscopy mmmm = content of isotactic polymer in the $^{13}$C-NMR spectrum in percent BD = polymer bulk density in $g/cm^3$ $d_{50}$ = average polymer particle diameter in $\mu m$ MFI/(230/5) = melt flow index, measured in accordance with DIN 53735; in g/10 minutes

SYNTHESIS OF THE METALLOCENES USED IN THE EXAMPLES

I) Metallocene A: rac-dimethylsilylbis{1-(2-methyl-4-ethylindenyl)}zirconium dichloride I.1. 4-Ethylindene (a2)

20.7 g (181.7 mmol) of 4-oxocaproaldehyde (a1, prepared from propionyl chloride and allyl chloride; cf. Synthesis, (1985) 1058) were dissolved in 10 ml of absolute methanol, and a solution of 13.2 g (199 mmol) of cyclopentadiene in 5 ml of absolute methanol was added, while cooling. This mixture was added dropwise to a solution of 51 g (454 mmol) of potassium tert-butylate in 100 ml of absolute methanol at 0° C. in the course of 35 minutes, during which a dark brown coloration occurred. After the mixture had been stirred at 0° C. for 2-4 hours and at room temperature for a further 2 hours, it was poured onto ice, the pH was brought to 6 and the mixture was extracted with methylene chloride. The organic phase was washed with saturated NaCl solution, dried over sodium sulfate and evaporated. The crude product was chromatographed on 750 g of silica gel 60. 11.1 g (43%) of the indene a2 (2 double bond isomers 3:2) could be isolated with hexane/methylene chloride (20:1 to 10:1).

I.2. 4-Ethyl-2-indanone (a3)

33.9 g (235 mmol) of 4-ethylindene (a2) were slowly added dropwise to a mixture of 141 ml of formic acid (98-100% strength) and 33 ml (340 mmol) of $H_2O_2$ (35% strength), while cooling with ice (highly exothermic reaction). The mixture was then stirred at room temperature for a further 2.5 hours. The yellow-orange suspension formed was freed from excess formic acid under a water pump vacuum. 900 ml of 2N sulfuric acid were added to the yellow oil which remained. A total of 3 l of water were distilled over, while topping up with water, the product separating out in the receiver as a yellowish oil. The distillate was neutralized with saturated sodium carbonate solution and extracted with ether. The ether phase was dried over sodium sulfate and evaporated. 22.4 g (59%) of the compound a3 were obtained as a white solid.

I.3. 2-Methyl-4-ethylindene (a4)

140 ml (420 mmol) of a 3M ethereal methylmagnesium bromide solution were added to a solution of 22.4 g (140 mmol) of a3 in 500 ml of diethyl ether at room temperature under Ar protection in the course of 1 hour. The mixture was then stirred under reflux at room temperature for another 2 hours, and was stirred at room temperature for a further 15 hours. The mixture was poured onto ice acidified with HCl, and extracted with ether. After the extract had been dried over sodium sulfate, the solvent was stripped off. The yellow oil which remained (20.3 g) was taken up in 800 ml of analytical grade toluene, 2.2 g (11.5 mmol) of p-toluenesulfonic acid hydrate were added and the mixture was refluxed for 45 minutes. After cooling, the solution was washed several times with water, dried over sodium sulfate and evaporated. The residue was chromatographed on 620 g of silica gel 60. 5.5 g (25%) of the indene a4 (yellowish oil) could be eluted with hexane/methylene chloride (20:1). Still unused starting material a3 could be recovered with hexane/ethyl acetate (9:1).

I.4. Dimethylsilylbis(2-methyl-4-ethylindene) (a5)

14 ml (34.8 mmol) of a 2.5M solution of n-butyllithium in hexane were slowly added to a solution of 5.5 g (34.8 mmol) of a4 in 30 ml of tetrahydrofuran under Ar protection at 0° C., and the mixture was then heated under reflux for 2 hours. The dark brown solution was then slowly added dropwise to a solution of 2.2 g (17.4 mmol) of dimethyldichlorosilane in 15 ml of tetrahydrofuran. The mixture was heated under reflux for a total of 10 hours and stirred overnight at room temperature, and was subsequently poured onto ice and extracted with diethyl ether. The residue which remained after the solvent had been stripped off was chromatographed on 200 g of silica gel. 2.0 g of unused starting material a4 were first eluted with hexane/methylene chloride (20:1 to 10:1). This was followed by 3.1 g of the product a5 (48% yield with respect to Si, 75% with respect to the educt reacted). The compound is obtained as a yellowish oil (2 isomers 3:1).

I.5. rac-Dimethylsilylbis{1-(2-methyl-4-ethylindenyl)}zirconium dichloride (A)

10 ml (25 mmol) of a 2.5M solution of butyllithium in hexane were added to a solution of 3.1 g (8.3 mmol) of the ligand system a5 in 30 ml of diethyl ether at room temperature under Ar protection. An orange coloration initially occurred, and after 45 minutes the solution became cloudy. After the mixture had been stirred overnight, 10 ml of hexane were added to the now beige-colored suspension and the mixture was filtered over a G3 frit. The precipitate was washed with 20 ml of hexane and dried under an oil pump vacuum for a long period of time. The virtually colorless powder was added rapidly to a suspension of 1.8 g (7.72 mmol) of zirconium tetrachloride in 30 ml of methylene chloride at −78° C. The mixture was warmed to room temperature in the course of 1-2 hours and, after stirring at room temperature for 30 minutes, was evaporated completely. The residue was dried under an oil pump vacuum and was first washed with 60 ml of hexane. The product was then isolated by extraction several times with a total of 180 ml of toluene. The combined extracts were concentrated and left to crystallize at −35° C. The first fraction gave 0.76 g of zirconocene A in the pure racemic form (orange-colored crystals). The subsequent fractions contained an increasing amount of the meso form. 1.78 g (43%) of compound A were isolated in total. $^1$H-NMR (CDCl$_3$) of the racemate: 6.85–7.55 (m,6,aromatic H), 6.80 (s,2,$\beta$-H), 2.72 (q,4,CH$_2$), 2.20 (s,6,CH$_3$), 1.30 (t,6,CH$_3$), 1.27 (s,6,Si-CH$_3$), $^1$H-NMR (CDCl$_3$) of the meso form: 6.6–7.6 (m,6,aromatic H), 6.68 (s,2,$\beta$-H), 2.7 (q,4,CH$_2$), 2.48 (s,6,CH$_3$), 1.13–1.43 (m,12,Et—CH$_3$,Si—CH$_3$).

II. Metallocene B: rac-dimethylsilylbis{1-(2-methyl-4-isopropylindenyl)}zirconium dichloride II.1. 4-Isopropylindene (b2)

5-Methyl-4-oxocaproaldehyde (b1) was prepared analogously to a1 by reaction of iso-butyryl chloride and allyl chloride (see I.1.). 45.6 g (356 mmol) of b1 were reacted with cyclopentadiene and potassium tert-butylate and the mixture was worked up, analogously to instructions I.1. Column chromatography gave 19.6 g (35%) of indene b2 as a yellow oil (2 double bond isomers).

II.2. 4-Isopropyl-2-indanone (b3)

33.8 g (213 mmol) of compound b2 were oxidized and the product was distilled with water, analogously to instructions I.2. 22.6 g (61%) of indanone b3 were obtained as a yellowish solid.

II.3. 2-Methyl-4-isopropylindene (b4)

11.1 g (63.8 mmol) of indanone b3 were reacted with 2.5 equivalents of methylmagnesium bromide analogously to instructions I.3. The reaction time was 17 hours at room temperature. The mixture was then refluxed with p-toluenesulfonic acid hydrate for 25 minutes. Chromatography gave 3.9 g (36%) of indene b4 as a colorless oil.

II.4.  Dimethylsilylbis(2-methyl-4-isopropylindene) (b5)

3.9 g (22.7 mmol) of indene b4 were reacted with dimethyldichlorosilane and the mixture was worked up, analogously to instructions I.4. Column chromatography gave, in addition to 0.44 g of unused indene, 3.0 g of product b5 as a yellow oil (isomers). The yield as 65% with respect to Si and 73% with respect to the starting material reacted.

II.5. rac-Dimethylsilylbis{1-(2-methyl-4-isopropylindenyl)}zirconium dichloride (B)

3.0 g of ligand system b5 were deprotonated and reacted with 1 equivalent of zirconium tetrachloride in 20 ml of methylene chloride, analogously to instructions I.5. After the crude product had been washed with 40 ml of hexane, the product was extracted with a total of 120 ml of toluene. The toluene extract was evaporated under an oil pump vacuum. 1.7 g (46%) of the zirconocene were obtained as an orange-colored powder. The racemate and the meso form were present in a ratio of 1:1. The racemic form could be isolated in the pure form by recrystallization from a little toluene or from toluene/hexane mixtures.

$^1$H-NMR of the racemate (CDCl$_3$): 6.7-7.5 (m,6,aromatic-H), 6.85 (s,2,$\beta$-H), 3.0 (m,2,i-Pr—CH) 2.23 (s,6,CH$_3$) 1.17-1.37 (d,12,i-Pr—CH$_3$) 1.27 (s,6,Si—CH$_3$).

$^1$H-NMR of the meso form (CDCl$_3$): 6.5-7.5 (m.6,aromatic-H) 6.75 (s,2,$\beta$-H) 3.0 (m,2,i-Pr—CH) 2.48 (s,6,CH$_3$) 1.10-1.45 (m,18,i-Pr—CH$_3$,Si—CH$_3$).

III. Metallocene C: rac-dimethylsilylbis{1-(2-methyl-4-tert-butylindenyl)}zirconium dichloride III.1. 4-tert-Butylindene (c2)

5,5-Dimethyl-4-oxocaproaldehyde c1 was prepared analogously to a1 by reaction of pivaloyl chloride and allyl chloride (see I.1.). 41 g (195 mmol) of c1 were reacted with cyclopentadiene and potassium tert-butylate and the mixture was worked up, analogously to instructions I.1. The reaction time was 19 hours at room temperature. Column chromatography gave 3.2 g (10%) of indene c2 as a yellow oil (2 double bond isomers).

III.2. 4-tert-Butyl-2-indanone (c3)

8.5 g (49.4 mmol) of compound c2 were oxidized and the product was distilled with water, analogously to instructions I.2. The reaction time was 4 hours at room temperature. 2.8 g (30%) of indanone c3 were obtained in the form of yellow crystals.

III.3. 2-Methyl-4-tert-butylindene (c4)

3.6 g (19 mmol) of indanone c3 were reacted with 3.0 equivalents of methylmagnesium bromide and the mixture was worked up, analogously to instructions I.3. The reaction time was 17 hours at room temperature and a further 4 hours under reflux. The mixture was then refluxed with p-toluenesulfonic acid hydrate for 25 minutes. Chromatography gave 1.2 g (33%) of indene c4 as a yellow oil. Unused starting material could be recovered with hexane/ethyl acetate (9:1).

III.4. Dimethylsilylbis(2-methyl-4-tert-butylindene) (c5)

1.2 g (6.4 mmol) of indene c4 were reacted with dimethyldichlorosilane and the mixture was worked up, analogously to instructions I.4. The reaction time was 10 hours under reflux and 3 days at room temperature. Column chromatography gave, in addition to 0.48 g of unused indene c4, 0.40 g of product c5 as a yellow oil (isomers). The yield was 29% with respect to Si and 49% with respect to starting material c4 reacted.

III.5.  rac-Dimethylsilylbis{1-(2-methyl-4-tert-butylindenyl)}zirconium dichloride (C)

0.74 ml (1.86 mmol) of a 2.5M solution of n-butyllithium in hexane was added to 0.40 g (0.93 mmol) of ligand system c5 in 9 ml of diethyl ether under Ar protection. After the mixture had been stirred overnight, the orange solution was evaporated completely. The residue was dried under an oil pump vacuum for a long time and added rapidly to a suspension of 225 mg (0.96 mmol) of zirconium tetrachloride in 5 ml of methylene chloride at $-78°$ C. The mixture was stirred at 0° C. for 2 hours and at room temperature for 30 minutes and evaporated completely. The product was extracted with a total of 8 ml of toluene. After the toluene had been stripped off, 210 mg (37%) of the zirconocene were obtained as an orange powder. The ratio of the racemate to the meso form was 1:1. The pure racemic form could be isolated by recrystallization from toluene/hexane.

$^1$H-NMR of the racemate (CDCl$_3$): 6.8-7.5 (m,6,aromatic-H) 6.92 (s,2,$\beta$-H) 2.27 (s,6,CH$_3$) 1.22-1.41 (m,24,t-Bu,Si—CH$_3$).

$^1$H-NMR of the meso form (CDCl$_3$): 6.7-7.6 (m,6,aromatic H) 6.7 (s,2,$\beta$-H) 2.50 (s,6,CH$_3$) 1.1-1.5 (m,24,t-Bu,Si—CH$_3$).

IV. Metallocene D: rac-methylphenylsilylbis{1-(2-methyl-4-isopropylindenyl)}zirconium dichloride IV.1. Methylphenylsilylbis(2-methyl-4-isopropylindene) (d5)

4.8 ml of a 2.5M solution of butyllithium in hexane were added to a solution of 2.0 g (11.8 mmol) of 2-methyl-4-isopropylindene b4 (see II.3.) in 40 ml of tetrahydrofuran under Ar protection at 0° C., and the mixture was heated under reflux for 90 minutes. The red solution was then added to a solution of 1.12 g (5.9 mmol) of methylphenyldichlorosilane in 15 ml of tetrahydrofuran, and the mixture was heated under reflux for 7 hours. It was poured onto ice and extracted with ether. The ether phase was dried over sodium sulfate and evaporated in vacuo. The residue which remained was chromatographed on 200 g of silica gel 60. 0.57 g of unused indene b4 was first recovered using a mobile phase mixture of hexane/methylene chloride (10:1). 1.2 g of product d5 followed using hexane/methylene chloride (10:2). The yield was 44% with respect to Si and 61% with respect to indene b4 reacted.

IV.2.  rac-Methylphenylsilylbis{1-(2-methyl-4-isopropylindenyl)}zirconium dichloride (D)

3.3 ml (8.3 mmol) of a 2.5M solution of butyllithium in hexane were slowly added to a solution of 1.28 g (2.76 mmol) of ligand system d5 in 20 ml of diethyl ether at room temperature under Ar protection, and the mixture was stirred overnight. The orange-colored solution was evaporated completely, dried under an oil pump vacuum for a long time and washed with a total of 20 ml of hexane. The residue was dried under an oil pump vacuum at 40° C. for a long time and powdered. The yellow powder was added to a suspension of 0.62 g (2.66 mmol) of zirconium tetrachloride in 15 ml of methylene chloride at $-78°$ C. The mixture was warmed to 0° C. in the course of 1 hour and stirred at room temperature for a further 2 hours. The red-brown suspension was evaporated completely and the residue was dried under an oil pump vacuum. 1.05 g (63%) of the zirconocene were extracted with toluene (orange powder). 1 racemic and 2 meso forms were present in the crude product in a ratio of 2:1:1. The racemic form could be isolated by recrystallization from toluene/hexane.

$^1$H-NMR of the isomer mixture (CDCl$_3$): 6.4–8.2 (m,aromatic-H,$\beta$-H) 3.1 (br,i-Pr—CH) 2.55 (s,CH$_3$) 2.33 (s,CH$_3$) 2.22 (s,CH$_3$) 1.95 (s,CH$_3$) 1.13–1.47 (m,i-Pr—CH$_3$,Si—CH$_3$).

V. Metallocene E: rac-dimethylsilylbis{1-(2-ethyl-4-methylindenyl)}zirconium dichloride V.1. 2-(2-Methylbenzyl)-butyric acid (e1)

14.2 g (0.62 mol) of sodium were dissolved in 250 ml of ethanol, and 118.4 g (0.63 mol) of diethyl ethylmalonate were added. 118.5 g (0.64 mol) of 2-methylbenzyl bromide were added dropwise such that the mixture boiled gently. The mixture was then heated under reflux for 4 hours. The suspension was poured into water and extracted with ether and the combined organic phases were dried over MgSO$_4$. The solvent was removed in vacuo and the resulting crude product (187 g) was subsequently reacted without further purification.

For hydrolysis, the product was heated under reflux in the presence of 139 g of KOH in 355 ml of ethanol and 170 ml of H$_2$O for 15 hours. The solvent mixture was stripped off in vacuo, and concentrated hydrochloric acid was added to the residue down to pH 1, while cooling. The mixture was extracted 3 times with ether, and the combined organic phases were washed with saturated aqueous NaCl solution and dried over MgSO$_4$. The solvent was removed and the residue was heated to 170° C. for decarboxylation, during which product e1 distilled off (140°–145° C./0.1 mmHg).

Yield: 96.0 g (81%).

V.2. 2-(2-methyl-benzyl)-butyryl chloride (e2)

96 g (0.5 mol) of 2-(o-xylyl)-butyric acid (e1) were heated slowly with 89 g (0.75 mol) of SOCl$_2$ and the mixture was refluxed until the evolution of gas had ended (1 h). Excess thionyl chloride was distilled off, and residues were removed by stripping off in each case 50 ml of toluene three times in vacuo. The crude product was purified by distillation (103° C./1 mmHg).

Yield: 101.7 g (96%, 0.48 mol).

V.3. 2-Ethyl-4-methyl-1-indanone (e3)

101.7 g (0.48 mol) of 2-(2-methyl-benzyl)-butyryl chloride (e2) were added dropwise to 191 g (1.43 mol) of AlCl$_3$ in 600 ml of toluene, and the mixture was heated at 80° C. for about 3.5 hours. The reaction mixture was poured onto 1 l of ice/concentrated HCl, and the phases were separated. The aqueous phase was extracted 4 times with 250 ml of toluene each time, and the combined organic phases were washed with saturated aqueous NaHCO$_3$ solution and NaCl solution and dried over MgSO$_4$. The solvent was removed in vacuo and the residue was distilled (78° C./0.2 mmHg).

Yield: 81 g (97%, 0.464 mmol).

V.4. 2-Ethyl-4-methyl-indene (e4)

11.1 g (294 mmol) of NaBH$_4$ were added in portions to 34.1 g (196 mmol) of 2-ethyl-4-methyl-1-indanone (e3) in 210 ml of tetrahydrofuran/methanol (2:1), and the mixture was stirred at room temperature for 15 hours. The reaction mixture was poured onto ice, and concentrated HCl was added to pH 1. After extraction with ether, the combined organic phases were washed with saturated aqueous NaHCO$_3$ solution and NaCl solution and dried over MgSO$_4$. The residue (36.2 g) which had been freed from the solvent in vacuo was further reacted directly for the subsequent elimination.

The non-purified 2-ethyl-4-methyl-1-indanol was treated on a steam bath in 700 ml of toluene in the presence of 0.75 g of p-toluenesulfonic acid monohydrate for 2 hours. The solvent mixture was removed in vacuo, the residue was taken up in ether, and the mixture was washed with saturated NaHCO$_3$ solution and NaCl solution and dried over MgSO$_4$. The solvent was removed in vacuo and the residue was distilled (62° C./0.2 mmHg).

Yield: 25.7 g (83%, 162 mmol).

V.5. Dimethylsilylbis(2-ethyl-4-methylindene) (e5)

26.2 ml (65.6 mmol) of a 2.5M solution of BuLi in hexane were slowly added dropwise to 10.4 g (65.5 mmol) of 2-ethyl-4-methyl-indene (e4) in 50 ml of absolute tetrahydrofuran, and stirring was continued at 50° C. for 2 hours. During this period, 3.95 ml of Me$_2$SiCl$_2$ were initially introduced into 50 ml of absolute tetrahydrofuran, and the Li salt was then added dropwise in the course of 8 hours. The mixture was stirred for 15 hours, the solvent was removed in vacuo and the residue was suspended in n-pentane and filtered off again. After the solvent mixture had been removed, the product was purified by column chromatography over silica gel (n-hexane/CH$_2$Cl$_2$ 9:1).

Yield: 15.1 g (63%, 41 mmol).

V.6. rac-Dimethylsilylbis{1-(2-ethyl-4-methylindenyl)}zirconium dichloride (E)

7.66 ml (19.16 mmol) of a 2.5M solution of BuLi in n-hexane were added dropwise at room temperature to 3.57 g (9.58 mmol) of Me$_2$Si(2-Et-4-Me—Ind)$_2$ in 50 ml of tetrahydrofuran, and the mixture was heated at 50° C. for a further 3 hours. It was evaporated to dryness, and the residue was suspended in n-pentane, filtered off and dried. 2.23 g (9.58 mmol) of ZrCl$_4$ were suspended in 150 ml of CH$_2$Cl$_2$ and the suspension was cooled to −78° C. The dilithium salt was added, and the mixture was stirred at −20° C. for 3 hours and allowed to come to room temperature overnight. The mixture was filtered and the solvent was removed. Crystallization from toluene/n-hexane (25:1) gave 0.18 g of orange crystals (meso/rac 5:1). The mother liquor was concentrated to ¼ of its volume and left to crystallize at −38° C., to give a further 0.1 g of the complex mixture. The mother liquor was evaporated to dryness, and the residue was suspended in n-hexane, filtered off and dried. The pure racemic form of E was obtained as an orange-colored powder.

VI. Metallocene F: rac-dimethylsilylbis{1-(2,4-dimethylindenyl)}zirconium dichloride VI.1. Methyl (±)-2-methyl-3-hydroxy-3-(2-tolyl)propionate (f1)

42 g (645 mmol) of Zn in 150 ml of toluene and 50 ml of Et$_2$O were heated to 80°–85° C., and a mixture of 51.6 g (430 mmol) of 2-tolyl-aldehyde and 62 ml (557 mmol) of bromo-2-methyl malon diethylester were added dropwise. After 5% of the malonate had been added, the heating was removed and an I$_2$ crystal was added. After vigorous foaming, the remainder was then added dropwise at 80°–85° C. in the course of 80 minutes, and the mixture was stirred at 85° C. for 2 hours and left to stand overnight.

200 g of ice/30 ml of H$_2$SO$_4$ were mixed and poured into the batch. After extraction with ether and washing of the organic phase with NaHCO$_3$ solution and NaCl solution, the product was dried and distilled (101° C./1 mmHg).

Yield: 86 g (96%).

VI.2. Methyl (±)-2-methyl-3-(2-tolyl)-propionate (f2)

132 ml (826 mmol) of HSiEt$_3$ were added to 86 g (413 mmol) of β-hydroxy ester f1 in 800 ml of CH$_2$Cl$_2$. 102 ml (826 mmol) of BF$_3$-ether were added in portions at −5°−−10° C. in the course of 5–10 minutes. After 20 hours at room temperature, the mixture was worked up. After hydrolysis with 220 ml of NaHCO$_3$ (pH 3), the mixture was extracted with ether, and the organic phase was separated off, washed with NaCl solution, dried and distilled (120° C./1 mmHg).

Yield: 58.9 g (74.1%).

VI.3. (±)-2-Methyl-3-(2-tolyl)-propionic acid (f3)

38.45 g (200 mmol) of ester f2, 850 ml of 5% strength NaOH and 850 ml of MeOH were refluxed for 4.5 hours, the MeOH was distilled off, the product was acidified, and the ether extract was dried with MgSO$_4$ and distilled (107°–109° C./high vacuum).

Yield: 31.8 g (89%).

VI.4. (±)-2-Methyl-3-(2-tolyl)-propionyl chloride (f4)

16.04 g (90 mmol) of acid f3 were heated slowly to 80° C. with 19.6 g (270 mmol) of SOCl$_2$ and kept at this temperature until the evolution of gas had ended. To remove the SOCl$_2$, the product was evaporated several times with toluene.

Yield: 17.7 g (crude)

VI.5. (±)-2,4-Dimethylindanone (f5)

36 g (270 mmol) of AlCl$_3$ were added to 17.7 g (90 mmol) of acid chloride f4 in 50 ml of toluene in the course of 20 minutes, and the mixture was stirred at 80° C. for 4 hours. It was poured onto ice/HCl, extracted with toluene, washed with H$_2$O, NaHCO$_3$ solution and NaCl solution, dried and distilled (109° C./1 mmHg) or chromatographed (n-hexane/ethyl acetate 6:1, r$_F$=0.44).

Yield: 13.75 g (95.4%).

Steps VI.1. to VI.5. were carried out analogously to those in Synth. Comm., 20 (1990) 1387–97.

VI.6. (±)-2,4-Dimethylindanol (f6)

3.55 g (93.9 mmol) of NaBH$_4$ were added in portions to 10.03 g (62.6 mmol) of ketone f5 in 150 ml of tetrahydrofuran/MeOH 2:1 at 0° C. in the course of 1 hour. The mixture was stirred at 0° C. for 2 hours and then at room temperature overnight. It was poured onto ice/HCl, the pH was brought to 1, any boric acid (?) which had precipitated at the phase boundary was filtered off, the mixture was extracted with Et$_2$O, and the extract was washed with NaHCO$_3$ solution and NaCl solution and dried using an oil pump.

Yield: 10.24 g

VI.7. 2,4-Dimethylindene (f7)

10.24 g (62 mmol) of indanol f6 were dissolved in toluene, and 20 mg of p-tolylsulfonic acid hydrate were added. The mixture was left to stand on a steam bath for 2.5 hours, a little water was added, the organic phase was evaporated off and the residue was distilled (133° C./10 mmHg).

Yield: 8.63 g (95%).

VI.8. (±)-Dimethylsilyl-bis(2,4-dimethylindene) (f8)

37.4 ml of a 1.6M (59.8 mmol) n-BuLi/n-hexane solution were added dropwise to 8.63 g (59.8 mmol) of ligand f7 in 100 ml of Et$_2$O, and the mixture was stirred at 40° C. for several hours. The Li salt was slowly added dropwise to 3.86 ml (29.9 mmol) of Me$_2$SiCl$_2$ in 30 ml of Et$_2$O, and the mixture was stirred for 2 hours. After filtration, the filtrate was evaporated and the residue was chromatographed (n-hexane/CH$_2$Cl$_2$ 9:1 r$_F$=0.29). The product fractions were combined and recrystallized from MeOH.

Yield: 1.25 g (12%).

VI.9. rac-Dimethylsilylbis{1-(2,4-dimethylindenyl)-}zirconium dichloride (F)

1.25 g (3.63 mmol) of chelate ligand f8 were dissolved in 20 ml of tetrahydrofuran, 2.9 ml of a 2.5M (7.26 mmol) n-BuLi/n-hexane solution were added dropwise and the mixture was stirred at −40° C. for 2 hours, until the evolution of butane had ended.

0.85 g (3.63 mmol) of ZrCl$_4$ was suspended in 30 ml of CH$_2$Cl$_2$. After addition of the dilithium salt at −78° C., the mixture was warmed slowly to room temperature, left to stand overnight and filtered. The filtrate was evaporated in vacuo. The complex was obtained as a mixture of the racemic with the meso form in a ratio of 1:1 (orange-colored powder). The pure racemic form could be isolated by recrystallization from toluene. Pure yield 15%.

$^1$H-NMR of the racemate (CDCl$_3$):6.8–7.5 (m,6,aromatic-H), 6.82 (s,2,β-H), 2.3 (s,6,CH$_3$), 2.1 (s,6,CH$_3$), 1.30 (s,6,Si—CH$_3$).

VII. Metallocene G: rac-dimethylsilylbis{1-(2-methyl-4-ethylindenyl)}zirconium-dimethyl 1.3 cm$^3$ of a 1.6M (2.08 mmol) ethereal solution of MeLi were added dropwise to 0.26 g of metallocene A in 40 cm$^3$ of Et$_2$O at −50° C., and the mixture was stirred at −10° C. for 2 hours. After the solvent had been replaced by n-pentane, the mixture was stirred at room temperature for a further 1.5 hours, and the residue was filtered off and sublimed in vacuo. 0.15 g of sublimate having a correct elemental analysis was obtained.

VIII. Reaction of metallocene G with [Bu$_3$NH][B(C$_6$H$_5$)$_4$]

0.15 g of metallocene G were added to 0.17 g of [Bu$_3$NH][B(C$_6$H$_5$)$_4$] in 25 cm$^3$ of toluene at 0° C. The mixture was heated to 50° C., while stirring, and stirred at this temperature for 10 minutes. The deep-colored mixture was then evaporated to dryness. An aliquot portion of the reaction mixture was used for the polymerization (Bu=butyl).

Abbreviations: Me=methyl, Et=ethyl, Bu=butyl, Ind=indenyl.

POLYMERIZATION EXAMPLES

Example 1

A dry 16 dm$^3$ reactor was flushed with nitrogen and filled with 10 dm$^3$ of liquid propylene.

30 cm$^3$ of a toluene solution of methylaluminoxane (corresponding to 45 mmol of Al, average degree of oligomerization n=16) were then added, and the batch was stirred at 30° C. for 15 minutes.

In parallel with this, 3.3 mg (0.006 mmol) of metallocene B were dissolved in 20 cm$^3$ of a toluene solution of methylaluminoxane (30 mmol of Al) and preactivated by being left to stand for 15 minutes.

The solution was then introduced into the reactor and heated up to the polymerization temperature of 70° C. (4° C./minute) by supplying heat, and the polymerization system was kept at 70° C. for 1 hour by cooling. The polymerization was stopped by addition of 20 ml of isopropanol. The excess monomer was gassed off and the polymer was dried in vacuo. 1.44 kg of polypropylene were obtained.

The catalyst activity was thus 436 kg of PP/g of metallocene×hour.

VN = 168 cm³/g;
m.p. = 149.6° C.; II = 95%;
mmmm = 88.6%;
BD = 0.30 g/cm³; d₅₀ = 2600 μm;
$M_w$ = 1.8 × 10⁵ g/mol;
$M_w/M_n$ = 2.2.

Examples 2-11

The procedure was in each case analogous to Example 1, but the following parameters were varied:
nature of the metallocene and
amount of the metallocene (mg)
polymerization temperature
The polymerization parameters varied and the polymer yield can be seen from Table 1, and the values measured on the polymers can be seen from Table 2.

TABLE 1

| Example | Metallocene Nature | Amount [mg] | Polymerization temperature [°C.] | Polymer yield [kg] |
|---|---|---|---|---|
| 2 | B | 3.1 | 60 | 0.82 |
| 3 | B | 6.4 | 50 | 1.30 |
| 4 | D | 10.1 | 30 | 0.75 |
| 5 | A | 4.4 | 70 | 1.10 |
| 6 | A | 6.3 | 50 | 0.55 |
| 7 | A | 6.1 | 30 | 0.25 |
| 8 | E | 3.0 | 70 | 0.50 |
| 9 | E | 2.7 | 50 | 0.26 |
| 10 | F | 3.0 | 70 | 0.72 |
| 11 | F | 10.3 | 50 | 0.96 |

TABLE 2

| Example | VN [cm³/g] | m.p. [°C.] | II [%] | mmmm [%] | BD g/cm³ | d₅₀ μm | $M_W$ [g/mol] | $M_W/M_n$ |
|---|---|---|---|---|---|---|---|---|
| 2 | 259 | 151.7 | n.m. | n.m. | 0.25 | 2500 | n.m. | n.m. |
| 3 | 354 | 152.4 | 97.9 | 91.6 | 0.24 | 600 | 4.6 × 10⁵ | 2.2 |
| 4 | 409 | 152.7 | n.m. | n.m. | n.m. | n.m. | 5.6 × 10⁵ | 2.4 |
| 5 | 131 | 145.1 | 96.0 | 88.0 | 0.35 | 2000 | 1.3 × 10⁵ | 2.1 |
| 6 | 215 | 150.1 | n.m. | n.m. | 0.15 | 3000 | n.m. | n.m. |
| 7 | 352 | 151.3 | n.m. | n.m. | n.m. | n.m. | n.m. | n.m. |
| 8 | 110 | 148.8 | 96.5 | 92.8 | 0.25 | 3500 | 1.2 × 10⁵ | 2.1 |
| 9 | 215 | 151.9 | 96.1 | 88.0 | n.m. | n.m. | 2.6 × 10⁵ | 2.3 |
| 10 | 123 | 146.0 | 94.9 | 87.0 | n.m. | n.m. | 1.2 × 10⁵ | 2.3 |
| 11 | 216 | 152.5 | n.m. | n.m. | n.m. | n.m. | n.m. | n.m. | n.m. = not measured

Example 12

The procedure was as in Example 1. However, directly after addition of the metallocene to the reactor, 0.3 bar of hydrogen was also forced into the reactor. 1.00 kg of polymer were obtained.
Vn = 76 cm³/g;
m.p.: = 148.9° C.;
BD = 0.20 g/cm³; d₅₀ = 1800 μm;
$M_w$ = 6.2 × 10⁴ g/mol;
$M_w/M_n$ = 2.8.

Example 13

A dry 16 dm³ reactor was flushed with nitrogen and filled with 10 dm³ of liquid propylene.
2.5 cm³ of reaction mixture according to Example VIII (corresponding to 15 mg of metallocene G) were then dissolved in 20 cm³ of toluene and the solution was introduced into the reactor at ambient temperature. The reactor was heated up to the polymerization temperature of 70° C. (4° C./minute) by supplying heat, and the polymerization system was kept at 70° C. for 1 hour by cooling. The polymerization was stopped by addition of 20 ml of isopropanol. The excess monomer was gassed off and the polymer was dried in vacuo. 0.8 kg of polypropylene was obtained.
VN = 120 cm³/g, m.p.: 144.8° C.

Example 14

A dry 70 dm³ reactor was flushed with nitrogen and filled with 40 dm³ of liquid propylene.
180 cm³ of a toluene solution of methylaluminoxane (corresponding to 270 mmol of Al, average degree of oligomerization n = 16) were then added and the batch was stirred at 30° C. for 15 minutes. 35 g of ethylene were then metered in. In parallel with this, 10.9 mg of metallocene A were dissolved in 20 cm³ of a toluene solution of methylaluminoxane (30 mmol of Al) and preactivated by being left to stand for 15 minutes.
The solution was then introduced into the reactor, and the reactor was heated up to the polymerization temperature of 50° C. in the course of 10 minutes by supplying heat, and kept at this temperature for 4 hours, while stirring. During the said 4 hours, a further 85 g of ethylene were metered in continuously. The polymerization was then stopped by addition of 20 ml of isopropanol, the excess monomer was gassed off and the polymer was dried in vacuo. 3.5 kg of random propylene-/ethylene copolymer having an ethylene content of 3.0% by weight were obtained.
VN = 226 cm³/g; $M_w$ = 2.3 × 10⁵ g/mol; $M_w/M_n$ = 1.9.

Example 15

A dry 16 dm³ reactor was flushed with nitrogen and filled at 20° C. with 10 dm³ of a dearomatized gasoline fraction having a boiling range of 100°-120° C.
The gas space of the vessel was then flushed free from nitrogen by forcing in 2 bar of ethylene and letting down 5 times.
30 cm³ of a toluene solution of methylaluminoxane (corresponding to 45 mmol of Al, molecular weight according to cryoscopic determination 750 g/mol) were then added.
The reactor contents were heated up to 30° C. in the course of 15 minutes, while stirring, and the overall pressure was brought to 5 bar by addition of ethylene at a stirring speed of 250 revolutions per minute.
In parallel with this, 2.3 mg of metallocene C were dissolved in 20 cm³ of a toluene solution of methylaluminoxane and preactivated by being left to stand for 15 minutes. The solution was then introduced into the reactor, and the polymerization system was brought to a temperature of 70° C. and kept at this temperature for 1 hour by appropriate cooling. The overall pressure during this time was kept at 5 bar by appropriate addition of ethylene.
The polymerization was stopped by addition of 20 ml of isopropanol, and the polymer was filtered off and dried in vacuo.
1.3 kg of polyethylene were obtained.
VN = 542 cm³/g.

We claim:
1. A process for the preparation of an olefin polymer by polymerization or copolymerization of an olefin of the formula $R^a$—CH=CH—$R^b$, in which $R^a$ and $R^b$ are identical or different and area hydrogen atom or a hydrocarbon radical having 1 to 14 carbon atoms, or $R^a$ and $R^b$ form a ring with the atoms joining them, at a temperature of −60° to 200° C., under a pressure of 0.5 to 100 bar, in solution, in suspension or in the gas phase, in the presence of a catalyst which is formed from a metallocene as the transition metal compound and a cocatalyst, which comprises using as the metallocene a compound of the formula I

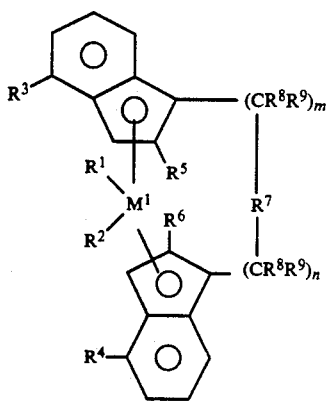

in which
M¹ is a metal of group IVb, Vb or VIb of the Periodic Table,
R¹ and R² are identical or different and are hydrogen, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group or a halogen atom,
R³ and R⁴ are identical or different and are a halogen atom, a $C_1$-$C_{10}$-alkyl group, which can be halogenated, a $C_6$-$C_{10}$-aryl group or an —$NR_2^{10}$, —$SR^{10}$, —$OSiR_3^{10}$, —$SiR_3^{10}$ or —$PR_2^{10}$ radical, in which $R^{10}$ is a halogen atom, a $C_1$-$C_{10}$-alkyl group or a $C_6$-$C_{10}$-aryl group,
R⁵ and R⁶ are identical or different and have the meaning mentioned for R³ and R⁴, and additionally can also be hydrogen,
R⁷ is

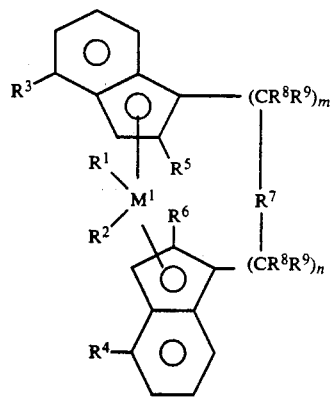

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$,
in which
$R^{11}$, $R^{12}$ and $R^{13}$ are identical or different and are a hydrogen atom, a halogen atom, a $C_1$-$C_{10}$-alkyl group, a $C_1$-$C_{10}$-fluoroalkyl group, a $C_6$-$C_{10}$-aryl group, a $C_6$-$C_{10}$-fluoroaryl group, a $C_1$-$C_{10}$-alkoxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group, or $R^{11}$ and $R^{12}$ or $R^{11}$ and $R^{13}$ in each case form a ring with the atoms joining them, or $R^{11}$ or $R^{12}$ with $R^8$ or $R^9$ in each case form a ring together with the atoms joining them,
M² is silicon, germanium or tin,
R⁸ and R⁹ are identical or different and have the meaning mentioned for $R^{11}$ and
m and n are identical or different and are zero, 1 or 2, m plus n being zero, 1 or 2.

2. A process as claimed in claim 1, wherein, in formula I, M¹ is Zr, R¹ and R² are identical or different and are methyl or chlorine, R³ and R⁴ are identical or different and are methyl, ethyl, n-propyl, i-propyl, n-butyl, i-butyl, tert-butyl or neopentyl, R⁵ and R⁶ are identical or different and are methyl or ethyl, R⁷ is a radical

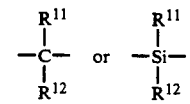

and n plus m is zero or 1.

3. The process as claimed in claim 1, wherein, in formula I, the substituents R¹ and R², R³ and R⁴, and R⁵ and R⁶ are in each case identical.

4. The process as claimed in claim 1, wherein the metallocene of the formula I used is rac-dimethylsilylbis(1-(2-methyl-4-ethylindenyl)-)zirconium dichloride, rac-dimethylsilylbis(1-(2-methyl-4-isopropylindenyl))zirconium dichloride, rac-dimethylsilylbis(1-(2-methyl-4-tert-butylindenyl))zirconium dichloride, rac-methylphenylsilylbis(1-(2-methyl-4-isopropylindenyl))zirconium dichloride, rac-dimethylsilylbis(1-(2-ethyl4-methylindenyl))zirconium dichloride, rac-dimethylsilylbis(1-(2,4-dimethylindenyl))zirconium dichloride or rac-dimethylsilylbis(1-(2-methyl-4-ethylindenyl))zirconium dimethyl.

5. The process as claimed in claim 1, wherein the cocatalyst used is an aluminoxane of the formula (II)

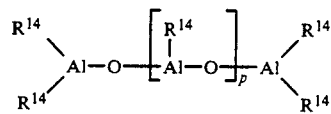

for the linear type and/or of the formula (III)

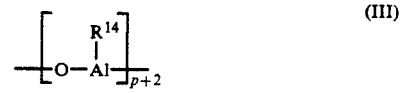

for the cyclic type,
in which, in the formulae (II) and (III), the radicals $R^{14}$ are identical or different and are a $C_1$-$C_6$-alkyl group, a $C_6$-$C_{18}$-aryl group or hydrogen and p is an integer from 2 to 50.

6. The process as claimed in claim 1, wherein the cocatalyst used is methylaluminoxane.

7. The process as claimed in claim 5, wherein the metallocene of the formula I is preactivated with an aluminoxane of the formula II and/or III before use in the polymerization reaction.

8. The process as claimed in claim 1, wherein said halogen is fluorine or chlorine.

9. The process as claimed in claim 1, wherein $M^1$ is zirconium, hafnium or titanium.

10. The process as claimed in claim 1, wherein $R^1$ and $R^2$ are identical or different and are a hydrogen atom, a $C_1$–$C_3$-alkyl group, a $C_1$–$C_3$-alkoxy group, a $C_6$–$C_8$-aryl group, a $C_6$–$C_8$-aryloxy group, a $C_2$–$C_4$-alkenyl group, a $C_7$–$C_{10}$-arylalkyl group, a $C_7$–$C_{12}$-alkylaryl group, a $C_8$–$C_{12}$-arylalkenyl group or a halogen atom.

11. The process as claimed in claim 1, wherein $R^3$ and $R^4$ are identical or different and are a chlorine atom, bromine atom, iodine atom, a $C_1$–$C_6$-alkyl group which can be halogenated or a $C_6$–$C_8$-aryl group.

12. The process as claimed in claim 1, wherein $R^5$ and $R^6$ are identical or different and are a $C_1$–$C_4$-alkyl which can be halogenated.

13. The process as claimed in claim 1, wherein $R^{11}$, $R^{12}$ and $R^{13}$ are identical or different and are a hydrogen atom, a halogen atom, a $C_1$–$C_4$-alkyl group, a $CF_3$ group, a $C_6$–$C_8$-aryl group, a pentafluorophenyl group, a $C_1$–$C_4$-alkoxy group, a $C_2$–$C_4$-alkenyl group, a $C_7$–$C_{10}$-arylalkyl group, a $C_8$–$C_{12}$-arylalkenyl group, a $C_7$–$C_{12}$-alkylaryl group or $R^{11}$ and $R^{12}$ or $R^{11}$ and $R^{13}$ in each case form a ring together with atoms adjoining them where $R^{11}$ or $R^{12}$ with $R^8$ or $R^9$ in each case form a ring together with atoms adjoining them.

14. The process as claimed in claim 1, wherein $M^2$ is silicon or germanium.

15. The process as claimed in claim 1, wherein $R^7$ is $=CR^{11}R^{12}$, $=SiR^{11}R^{12}$, $=GeR^{11}R^{12}$, $-O-$, $-S-$, $=SO$, $=PR^{11}$ or $=P(O)R^{11}$.

16. The process as claimed in claim 1, wherein m and n are identical or different and are 0 or 1, and m+n are 0 or 1.

17. The process as claimed in claim 1, wherein the reaction temperature is from $-40°$ C. to $100°$ C.

18. The process as claimed in claim 17, wherein the reaction temperature is from $0°$ C. to $25°$ C.

19. The process as claimed in claim 1, wherein the reaction time is between 10 minutes and 100 hours.

20. The process as claimed in claim 5, wherein p is an integer from 10 to 35.

* * * * *

UNITED STATES PATENT AND TRADEMARK OFFICE
CERTIFICATE OF CORRECTION

PATENT NO. : 5,278,264
DATED : January 11, 1994
INVENTOR(S) : Spaleck et al.

It is certified that error appears in the above-identified patent and that said Letters Patent is hereby corrected as shown below:

In claim 1, column 21, lines 40 through 55 should read --
$R^7$ is

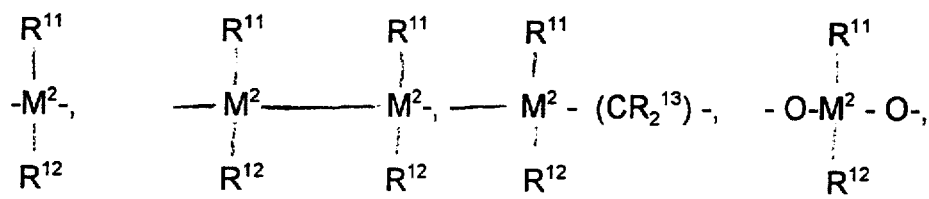

In claim 4, at column 22, line 28 should read - - rac-dimethylsilylbis(1-(2-methyl-4-ethylindenyl)}--

In claim 4, at column 22, line 29, ")zirconium dichloride" should read - - zirconium dichloride- - .

UNITED STATES PATENT AND TRADEMARK OFFICE
CERTIFICATE OF CORRECTION

PATENT NO. : 5,278,264
DATED : January 11, 1994
INVENTOR(S) : Spaleck et al.

It is certified that error appears in the above-identified patent and that said Letters Patent is hereby corrected as shown below:

In claim 4, at column 22, line 9 should read --dichloride, rac-dimethylsilylbis (1-(2-ethyl-4- --

Signed and Sealed this

Second Day of May, 2000

Q. TODD DICKINSON

*Attest:*

*Attesting Officer*  *Director of Patents and Trademarks*